United States Patent
Levy et al.

(10) Patent No.: US 12,246,195 B2
(45) Date of Patent: Mar. 11, 2025

(54) PRE-TREATMENT TISSUE SENSITIZATION FOR FOCUSED ULTRASOUND PROCEDURES

(71) Applicant: INSIGHTEC, LTD., Tirat Carmel (IL)

(72) Inventors: Yoav Levy, Hinanit (IL); Israel Schuster, Kiryat Tivon (IL); Shahar Rinott, Haifa (IL)

(73) Assignee: INSIGHTEC, LTD., Tirat Carmel (IL)

( * ) Notice: Subject to any disclaimer, the term of this patent is extended or adjusted under 35 U.S.C. 154(b) by 0 days.

(21) Appl. No.: 17/768,177

(22) PCT Filed: Oct. 12, 2020

(86) PCT No.: PCT/IB2020/000845
§ 371 (c)(1),
(2) Date: Apr. 11, 2022

(87) PCT Pub. No.: WO2021/069971
PCT Pub. Date: Apr. 15, 2021

(65) Prior Publication Data
US 2024/0091565 A1     Mar. 21, 2024

Related U.S. Application Data

(60) Provisional application No. 62/913,772, filed on Oct. 11, 2019.

(51) Int. Cl.
*A61N 7/02* (2006.01)
*A61B 90/00* (2016.01)
*A61N 7/00* (2006.01)

(52) U.S. Cl.
CPC .......... *A61N 7/02* (2013.01); *A61B 2090/374* (2016.02); *A61N 2007/0039* (2013.01); *A61N 2007/0095* (2013.01)

(58) Field of Classification Search
CPC .............. A61N 7/02; A61N 2007/0039; A61N 2007/0095; A61B 2090/374
See application file for complete search history.

(56) References Cited

U.S. PATENT DOCUMENTS

2007/0055155 A1* 3/2007 Owen ...................... A61B 8/00
600/439
2007/0161897 A1 7/2007 Sasaki et al.
(Continued)

FOREIGN PATENT DOCUMENTS

JP    2007/007279 A   1/2007
WO   2004/100811 A1  11/2004
(Continued)

OTHER PUBLICATIONS

Office Action issued in corresponding Japanese Application No. 2022-521300, dated May 17, 2023, 21 pages.
(Continued)

*Primary Examiner* — Sean A Frith
(74) *Attorney, Agent, or Firm* — Morgan, Lewis & Bockius LLP

(57) ABSTRACT

Systems and methods for treating target tissue include generating a priming sequence of sonication pulses for delivering acoustic energy to the target tissue; pausing generation of the sonication pulses for a delay interval; and generating a series of treatment sequences of sonication pulses for delivering acoustic energy to the target tissue, the treatment sequences having sonication intervals therebetween and the delay interval being larger than the largest sonication interval by a predetermined factor.

31 Claims, 9 Drawing Sheets

(56) References Cited

U.S. PATENT DOCUMENTS

| | | | | |
|---|---|---|---|---|
| 2010/0081971 A1* | 4/2010 | Allison | ............ | A61F 7/00 |
| | | | | 606/1 |
| 2011/0009734 A1* | 1/2011 | Foley | ............ | A61N 7/02 |
| | | | | 601/2 |
| 2011/0208113 A1* | 8/2011 | Toma | ............ | A61N 7/022 |
| | | | | 435/174 |
| 2013/0204316 A1* | 8/2013 | Carpentier | ............ | A61B 8/56 |
| | | | | 607/45 |
| 2015/0011916 A1* | 1/2015 | Cannata | ............ | A61N 7/00 |
| | | | | 601/2 |
| 2017/0151448 A1* | 6/2017 | Yon | ............ | A61N 7/02 |
| 2019/0232090 A1* | 8/2019 | Ben-Ezra | ............ | A61B 90/50 |
| 2019/0329075 A1* | 10/2019 | Sutton | ............ | A61B 5/0036 |

FOREIGN PATENT DOCUMENTS

| | | | |
|---|---|---|---|
| WO | 2015/200576 A1 | 12/2015 | |
| WO | WO-2016004437 A1 * | 1/2016 | ............ A61N 7/00 |
| WO | WO2018/215839 A2 | 11/2018 | |
| WO | WO2019/116097 A1 | 6/2019 | |

OTHER PUBLICATIONS

Insightec Ltd., International Search Report and Written Opinion corresponding to International Application No. PCT/IB2020/000845, dated Feb. 8, 2021, 15 pgs.

Insightec Ltd., Communication Pursuant to Rules 161(1) and 162, EP20804329.9, May 18, 2022, 3 pgs.

\* cited by examiner

PRE-TREATMENT TISSUE SENSITIZATION FOR FOCUSED ULTRASOUND PROCEDURES

CROSS-REFERENCE TO RELATED APPLICATION

This application is a United States National Stage Application filed under 35 U.S.C. § 371 of PCT Patent Application Serial No. PCT/IB2020/000845, filed on Oct. 12, 2020, which claims priority to and the benefit of, U.S. Provisional Patent Application No. 62/913,772, filed on Oct. 11, 2019, each of which is hereby incorporated by reference in its entirety.

FIELD OF THE INVENTION

The present invention relates, in general, to ultrasound therapy, and, in particular, to systems and methods for enhancing tissue response during the ultrasound therapy.

BACKGROUND

Tissue, such as a benign or malignant tumor, organ, or other body region may be treated invasively by surgically removing the tissue, or with minimal intrusion or fully non-invasively by using, for example, thermal ablation. Both approaches may effectively treat certain localized conditions, but involve delicate procedures to avoid destroying or damaging otherwise healthy tissue.

Thermal ablation, as may be accomplished using focused ultrasound, has particular appeal for treating diseased tissue surrounded by or neighboring healthy tissue or organs because the effects of ultrasound energy can be confined to a well-defined target region. Ultrasonic energy may be focused to a zone having a cross-section of only a few millimeters due to relatively short wavelengths (e.g., as small as 1.5 millimeters (mm) in cross-section at one Mega-Hertz (1 MHz)). Moreover, because acoustic energy generally penetrates well through soft tissues, intervening anatomy often does not impose an obstacle to defining a desired focal zone. Thus, ultrasonic energy may be focused at a small target in order to ablate diseased tissue while minimizing damage to surrounding healthy tissue.

To focus ultrasonic energy at a desired target, drive signals may be sent to an acoustic (preferably piezoelectric) transducer having a number of transducer elements such that constructive interference occurs at the focal zone. At the target, sufficient acoustic energy may be delivered to heat tissue until necrosis occurs, i.e., until the tissue is destroyed. Preferably, non-target tissue along the path through which the acoustic energy passes (the "pass zone") outside the focal zone is heated only minimally, if at all, thereby minimizing damage to tissue outside the focal zone.

Typically, ultrasonic energy is delivered according to a treatment plan, often based on a predefined model of the target and the patient's anatomy. During treatment, the temperature at the target is monitored using, for example, a magnetic resonance imaging (MRI) apparatus. If the measured temperature is below the desired target temperature for necrosis, the ultrasonic energy transmitted from the transducer is increased. In some situations, however, the maximum acoustic energy deliverable to a target is limited—due, for example, to heat sensitivity of surrounding tissue.

Accordingly, there is a need for approaches that provide effective ultrasound therapy without exceeding the maximum allowable deposit of acoustic energy and consequent injury to non-target tissue.

SUMMARY

The present invention provides systems and methods for permitting effective ultrasound therapy of the target tissue while avoiding damage to non-target tissue by increasing tissue sensitivity in the target region prior to performing an ultrasound therapy. In various embodiments, a "priming" stage that applies one or more sequences of sonications to the target tissue is performed prior to exposure of the target tissue to a series of one or more sequences of therapeutic sonications. The priming sequence of sonications may efficiently enhance sensitivity of various types of tissue in the target to acoustic energy at various frequencies. Because the tissue sensitivity at the target region is increased, the minimum acoustic energy required for tissue necrosis therein can be reduced. As a result, acoustic energy transmitted from the ultrasound transducer may be reduced to provide effective target therapy without exceeding the maximum allowable deposit of acoustic energy and consequent injury to non-target tissue.

In one embodiment, after the priming sequence(s) of sonications ends, the ultrasound transducer is halted for a delay interval prior to application of the series of one or more therapeutic sonication sequences. In addition, the delay interval is preferably longer than the longest sonication interval between two consecutive therapeutic sonication sequences by a predetermined factor (e.g., 2 times, 10 times, 50 times or 100 times). Additionally or alternatively, small gas/liquid bubbles (or "microbubbles") may be introduced to the target region prior to and/or during the priming stage; cavitation of the microbubbles may further enhance tissue sensitivity in the target region. In some embodiments, the microbubbles are introduced to the target after the priming sequence (e.g., during treatment) to assist tissue disruption or necrosis and/or improve focusing properties of the ultrasound focused beam.

Accordingly, in one aspect, the invention pertains to a system for treating target tissue. In various embodiments, the system includes an ultrasound transducer (e.g., a phased-array transducer) for delivering acoustic energy to the target tissue; and a controller, configured to (i) generate a priming sequence of sonication pulses for driving the ultrasound transducer to deliver acoustic energy to the target tissue in accordance with the priming sequence, (ii) pause driving the ultrasound transducer for a delay interval, and (iii) generate a series of treatment sequences of sonication pulses for driving the ultrasound transducer to deliver acoustic energy to the target tissue in accordance with the series of treatment sequences. In one implementation, the treatment sequences have sonication intervals therebetween and the delay interval is larger than the largest sonication interval by a predetermined factor (e.g., 2 times or 10 times).

In addition, the system may further include an administration device for administering an ultrasound contrast agent for action at the target tissue. For example, the controller may be further configured to operate the administration device to administer the ultrasound contrast agent during the priming sequence and/or the treatment sequence. In some embodiments, the priming sequence has one or more fixed parameters selected from a frequency, a power, a mechanical index in the target tissue and an acoustic beam shape. The controller may be further configured to determine the value(s) of the fixed parameter(s) for maintaining a target concentration of microbubbles at the target tissue. Additionally or alternatively, the controller may be further configured to determine the value(s) of the fixed parameter(s) for maintaining a target concentration of microbubbles at the target tissue.

In various embodiments, the priming sequence has one or more varying parameter selected from a frequency, a power, a mechanical index in target tissue and an acoustic beam shape. The controller may be further configured to determine the value(s) of the varying parameter(s) for (i) initiating microbubble cavitation in the target tissue, (ii) maintaining a target range of microbubble cavitation at the target tissue, and/or (iii) avoiding formation of a microbubble cloud in the target tissue. In one embodiment, the controller is further configured to determine the target range of microbubble cavitation based at least in part on an acoustic response from the target tissue.

Additionally, the system may further include one or more acoustic-signal detectors; the controller may be further configured to adjust a parameter associated with the priming sequence based on an acoustic response from the target tissue detected by the acoustic-signal detector(s). In one implementation, the priming sequence has a mixed frequency. Further, the system may include one or more imaging devices (e.g., an ultrasound, an MRI, a CT, an X-Ray, a PET, an SPECT or an infrared imaging device) for guiding the priming sequence and/or the treatment sequences. The imaging device may produce 1D, 2D, 3D and/or 4D images.

In another aspect, the invention relates to a method of treating target tissue. In various embodiments, the method includes generating a priming sequence of sonication pulses for delivering acoustic energy to the target tissue; pausing generation of the sonication pulses for a delay interval; and generating a series of treatment sequences of sonication pulses for delivering acoustic energy to the target tissue. In one implementation, the treatment sequences have sonication intervals therebetween and the delay interval is larger than the largest sonication interval by a predetermined factor.

Another aspect of the invention relates to a system for treating target tissue. In various embodiments, the system includes an ultrasound transducer (e.g., a phased-array transducer) for delivering acoustic energy to the target tissue; an administration device for administering an ultrasound contrast agent at the target tissue; and a controller, configured to (i) generate a priming sequence of sonication pulses for driving the ultrasound transducer to deliver acoustic energy to the target tissue in accordance with the priming sequence, (ii) operate the administration device to administer the ultrasound contrast agent during the priming sequence, and (iii) generate a treatment sequence of sonication pulses for driving the ultrasound transducer to deliver acoustic energy to the target tissue in accordance with the treatment sequence.

In various embodiments, the priming sequence has one or more fixed parameter selected from a frequency, a power, a mechanical index in the target tissue and an acoustic beam shape. In addition, the controller may be further configured to determine the value(s) of the fixed parameter(s) for maintaining a target concentration of microbubbles at the target tissue. In one embodiment, the priming sequence has one or more varying parameters selected from a frequency, a power, a mechanical index in target tissue and an acoustic beam shape. The controller is further configured to determine the value(s) of the varying parameter(s) for (i) initiating microbubble cavitation in the target tissue, (ii) maintaining a target range of microbubble cavitation at the target tissue, and/or (iii) avoiding formation of a microbubble cloud in the target tissue. Further, the controller may be further configured to determine the target range of microbubble cavitation based at least in part on an acoustic response from the target tissue.

In some embodiments, the system further includes one or more acoustic-signal detectors; the controller is further configured to adjust a parameter associated with the priming sequence based on an acoustic response from the target tissue detected by the acoustic-signal detector(s). In one embodiment, the priming sequence has a mixed frequency. In addition, the system may further include one or more imaging devices (e.g., an ultrasound, an MRI, a CT, an X-Ray, a PET, an SPECT or an infrared imaging device) for guiding the priming sequence and/or the treatment sequence. The imaging device(s) may produce 1D, 2D, 3D and/or 4D images. In one implementation, the controller is further configured to operate the administration device to administer the ultrasound contrast agent during the treatment sequence.

In yet another aspect, the invention pertains to method of treating target tissue. In various embodiments, the method includes generating a priming sequence of sonication pulses for delivering acoustic energy to the target tissue in accordance with the priming sequence; administering an ultrasound contrast agent during the priming sequence; and generating a treatment sequence of sonication pulses for delivering acoustic energy to the target tissue in accordance with the treatment sequence.

As used herein, the term "substantially" means ±10%, and in some embodiments, ±5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

DETAILED DESCRIPTION

Figure 1A:
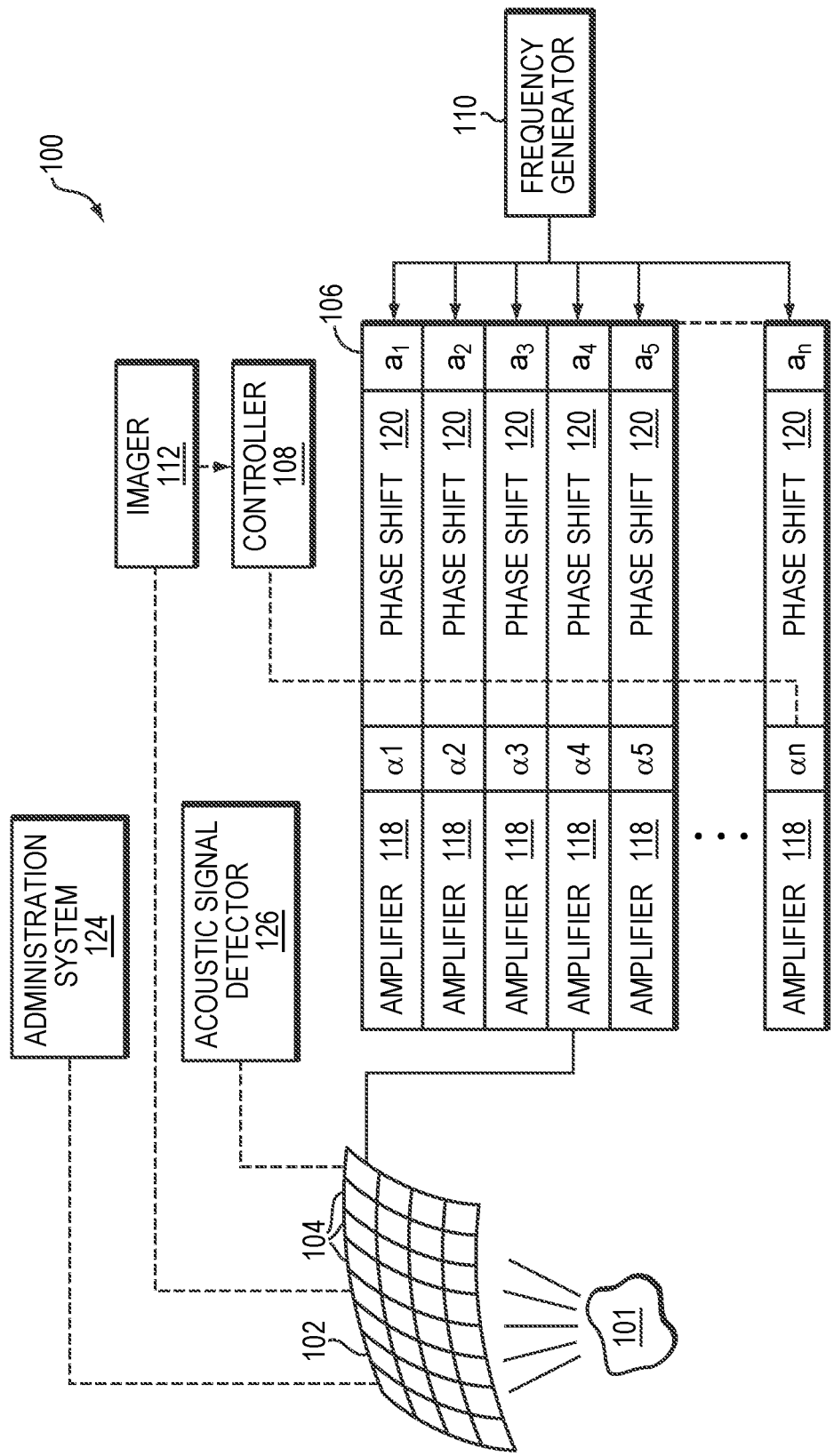
FIG. 1A illustrates a focused ultrasound system in accordance with various embodiments of the current invention.

FIG. 1A illustrates an exemplary ultrasound system 100 for focusing ultrasound onto a target region 101 in a patient. The system 100 can shape the ultrasonic energy in various ways, producing, for example, a point focus, a line focus, a ring-shaped focus, or multiple foci simultaneously. In various embodiments, the system 100 includes a phased array 102 of transducer elements 104, a beamformer 106 driving the phased array 102, a controller 108 in communication with the beamformer 106, and a frequency generator 110 providing an input electronic signal to the beamformer 106.

The array 102 may have a curved (e.g., spherical or parabolic) shape suitable for placing it on the surface of a skull or a body part other than the skull, or may include one or more planar or otherwise shaped sections. Its dimensions may vary, depending on the application, between millimeters and tens of centimeters. The transducer elements 104 of the array 102 may be piezoelectric ceramic, capacitive micromachined ultrasonic transducer (CMUT) or microelectromechanical systems (MEMS) elements, and may be mounted in silicone rubber or any other material suitable for damping the mechanical coupling between the elements 104. Piezo-composite materials, or generally any materials shaped in a manner facilitating conversion of electrical energy to acoustic energy, may also be used. To assure maximum power transfer to the transducer elements 104, the elements 104 may be configured for electrical resonance, matching input impedance.

The transducer array 102 is coupled to the beamformer 106, which drives the individual transducer elements 104 so that they collectively produce a focused ultrasonic beam or field. For n transducer elements, the beamformer 106 may contain n driver circuits, each circuit including or consisting of an amplifier 118 and a phase shift circuit 120; drive circuit drives one of the transducer elements 104. The beamformer 106 receives a radio frequency (RF) input signal, typically in the range from 0.1 MHz to 4.0 MHz, from the frequency generator 110, which may, for example, be a Model DS345 generator available from Stanford Research Systems. The input signal may be split into n channels for the n amplifiers 118 and delay circuits 120 of the beamformer 106. In some embodiments, the frequency generator 110 is integrated with the beamformer 106. The radio frequency generator 110 and the beamformer 106 are configured to drive the individual transducer elements 104 of the transducer array 102 at the same frequency, but at different phases and/or different amplitudes.

The amplification or attenuation factors $\alpha_1$-$\alpha_n$ and the phase shifts $a_1$-$a_n$ imposed by the beamformer 106 serve to transmit and focus ultrasonic energy through inhomogeneous tissue (e.g., the patient's skull or different tissues located in the acoustic paths of ultrasound beams from the transducer elements to the target region or "path zones") onto the target region (e.g., a region in the patient's brain). Via adjustments of the amplification factors and/or the phase shifts, a desired shape and intensity of a focal zone may be created at the target region.

The amplification factors and phase shifts may be computed using the controller 108, which may provide the relevant computational functions through software, hardware, firmware, hardwiring, or any combination thereof. For example, the controller 108 may utilize a general-purpose or special-purpose digital data processor programmed with software in a conventional manner, and without undue experimentation, to determine the frequency, phase shifts and/or amplification factors of the transducer elements 104. In certain embodiments, the controller computation is based on information about the characteristics (e.g., structure, thickness, density, etc.) of intervening tissues located between the transducer 102 and the target 101 (e.g., the pass zone) and their effects on propagation of acoustic energy. In various embodiments, such information is obtained from an imager 112, such as a magnetic resonance imaging (MRI) device, a computer tomography (CT) device, a positron emission tomography (PET) device, a single-photon emission computed tomography (SPECT) device, or an ultrasonography device. Image acquisition may be three-dimensional (3D) or, alternatively, the imager 112 may provide a set of two-dimensional (2D) images suitable for reconstructing a three-dimensional image of the target region 101 and/or other regions (e.g., the region surrounding the target 101, the region in the pass zone located between the transducer and the target, or another target region). Image-manipulation functionality may be implemented in the imager 112, in the controller 108, or in a separate device.

In addition, the ultrasound system 100 may include an administration system 124 for introducing microbubbles into the patient's body. Examples of suitable administration systems are described in PCT Publication No. WO 2019/116095, the entire contents of which are incorporated herein by reference. In some embodiments, the ultrasound system 100 and/or imager 112 can be utilized to detect signals from the microbubbles located at or close to (e.g., within 10 mm of) the target region 101 so as to identify the amount, type and/or location of the microbubble cavitation. Additionally or alternatively, the system 100 may include an acoustic-signal detector (such as a hydrophone or suitable alternative) 126 that detects transmitted and/or reflected ultrasound from the microbubbles, and which may provide the signals it receives to the controller 108 for further processing. Approaches to utilizing reflection signals from the microbubbles for identifying the amount, type and/or location of the microbubble cavitation are provided, for example, in U.S. Pat. No. 10,575,816, the entire content of which is incorporated herein by reference. The imager 112, the administration system 124, and/or the acoustic-signal detector 126 may be operated using the same controller 108 that governs the transducer operation; alternatively, they may be separately controlled by one or more dedicated controllers intercommunicating with one another.

Figure 1B:
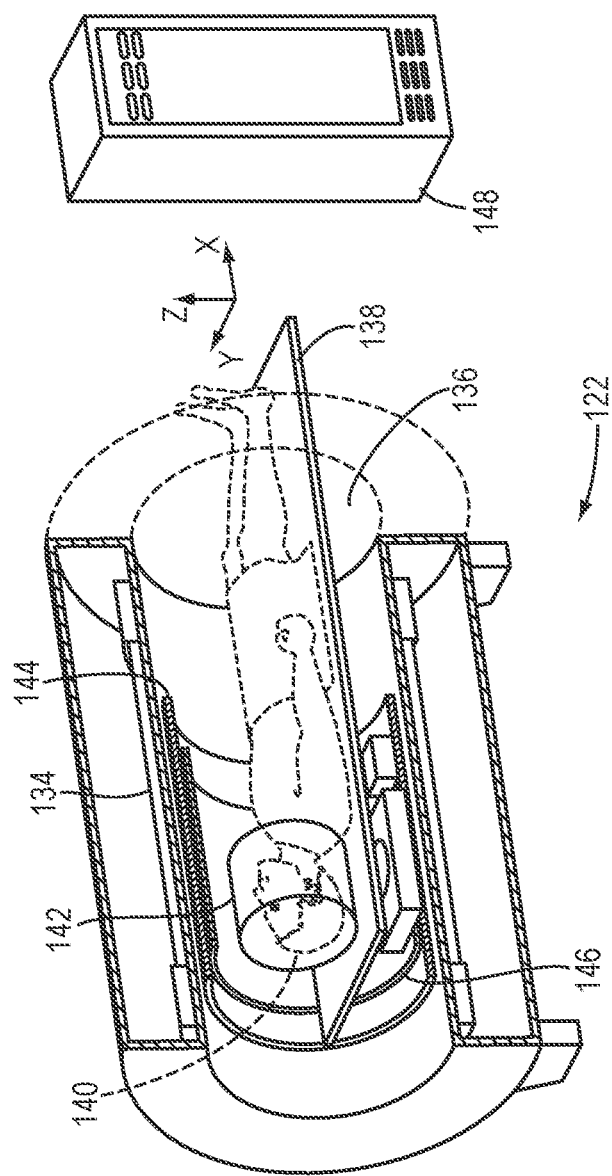
FIG. 1B schematically depicts an exemplary MRI system in accordance with various embodiments of the current invention.

FIG. 1B illustrates an exemplary imager—namely, an MRI apparatus 112. The apparatus 112 may include a cylindrical electromagnet 134, which generates the requisite static magnetic field within a bore 136 of the electromagnet 134. During medical procedures, a patient is placed inside the bore 136 on a movable support table 138. A region of interest 140 within the patient (e.g., the patient's head) may be positioned within an imaging region 142 wherein the electromagnet 134 generates a substantially homogeneous field. A set of cylindrical magnetic field gradient coils 144 may also be provided within the bore 136 and surrounding the patient. The gradient coils 144 generate magnetic field gradients of predetermined magnitudes, at predetermined times, and in three mutually orthogonal directions. With the field gradients, different spatial locations can be associated with different precession frequencies, thereby giving an MR image its spatial resolution. An RF transmitter coil 146 surrounding the imaging region 142 emits RF pulses into the imaging region 142 to cause the patient's tissues to emit magnetic-resonance (MR) response signals. Raw MR response signals are sensed by the RF coil 146 and passed to an MR controller 148 that then computes an MR image, which may be displayed to the user. Alternatively, separate MR transmitter and receiver coils may be used. Images acquired using the MRI apparatus 112 may provide radiologists and physicians with a visual contrast between different tissues and detailed internal views of a patient's anatomy that cannot be visualized with conventional x-ray technology.

The MRI controller 148 may control the pulse sequence, i.e., the relative timing and strengths of the magnetic field gradients and the RF excitation pulses and response detection periods. The MRI controller 148 may be combined with the transducer controller 108 into an integrated system control facility.

The MR response signals are amplified, conditioned, and digitized into raw data using a conventional image-processing system, and further transformed into arrays of image data by methods known to those of ordinary skill in the art. The image-processing system may be part of the MRI controller 148, or may be a separate device (e.g., a general-purpose computer containing image-processing software) in communication with the MRI controller 148 and/or the transducer controller 108. Because the response signal is tissue- and temperature-dependent, it can be processed to identify the treatment target region (e.g., a tumor to be destroyed by heat) 101 in the image, as well as to compute a temperature map from the image. Further, the acoustic field resulting from ultrasound application may be monitored in real time, using, e.g., thermal MRI or MR-based acoustic radiation force imaging. Thus, using MRI data, the ultrasound transducer 102 may be driven so as to focus ultrasound into (or near) the target region 101, while the temperature of the target and surrounding tissues and/or the acoustic field intensity are being monitored.

In an exemplary procedure, the imager (e.g., MRI device) 112 acquires information (such as the location, size and/or shape) of the target region and/or non-target region prior to applying ultrasound sonications. In one embodiment, the information includes a 3D set of voxels corresponding to the target/non-target regions, and in some cases, the voxels include attributes specifying tissue characteristics (e.g., the type, property, structure, thickness, density, etc.). Based on the acquired information, the transducer configurations (e.g., frequency, phase and/or amplitude) can be determined to create a focus at the target region 101 without overheating the non-target region.

Figure 2A:
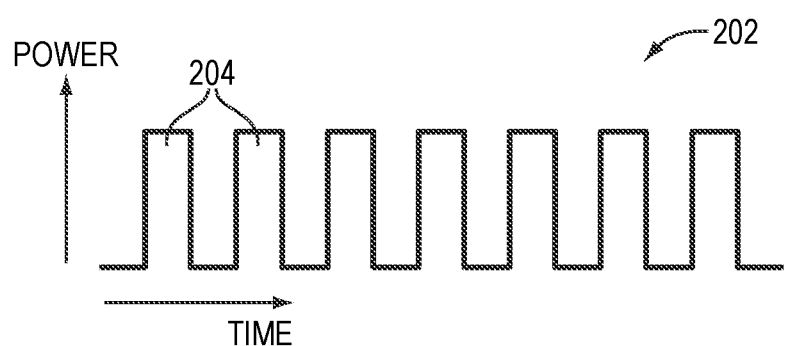
FIG. 2A depicts a single continuous priming sequence of sonication pulses in accordance with various embodiments of the current invention.
Figure 2B:
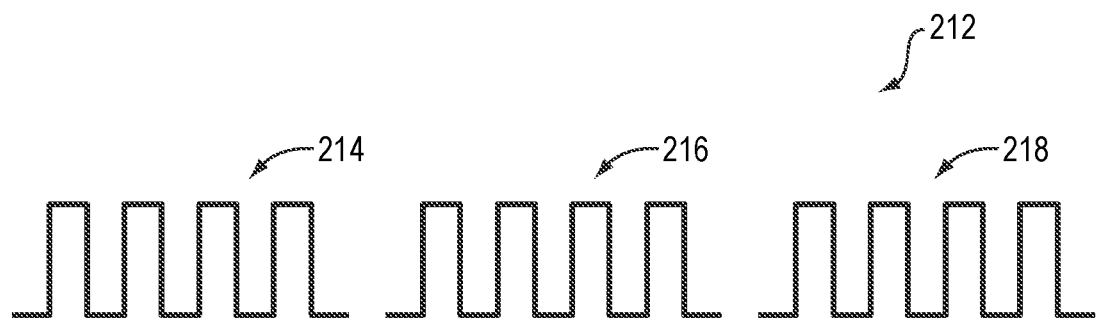
FIG. 2B depicts a series of time-separated priming sequences of sonication pulses in accordance with various embodiments of the current invention.

In various embodiments, once the target/non-target region is characterized, a priming stage involving application of at least one sequence of sonications to the target tissue is performed prior to exposure of the target tissue to a series of therapeutic sonications. Referring to FIG. 2A, the priming sequence may consist of a single continuous sequence 202 of sonication pulses 204 (at the frequency to be used during treatment). In one embodiment, the single continuous pulse sequence 202 lasts from 0.01 to 10 sec. Alternatively, referring to FIG. 2B, the priming sequence may include a series 212 of time-separated pulse sequences 214-218 (e.g., a 16 ms burst repeated at a frequency of 10 Hz, also at the same ultrasound frequency as will be used during treatment). The series 212 of time-separated pulse sequences 214-218 may collectively last from 1 to 600 sec.

Figure 3A:
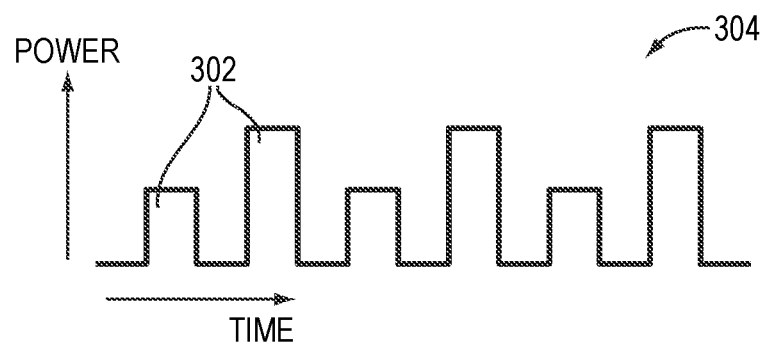
FIGS. 3A-3I depict various configurations of one or more priming sequences of sonication pulses in accordance with various embodiments of the current invention.
Figure 3B:
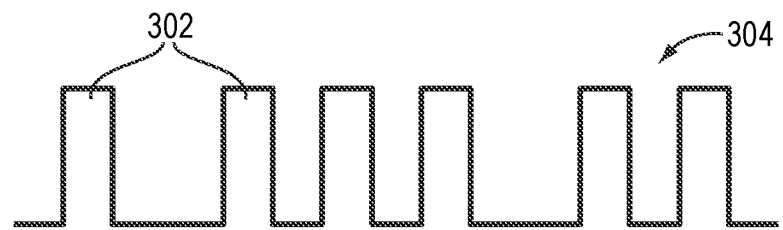
Figure 3C:
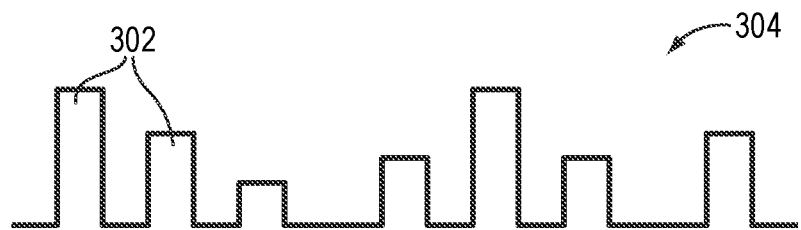
Figure 3D:
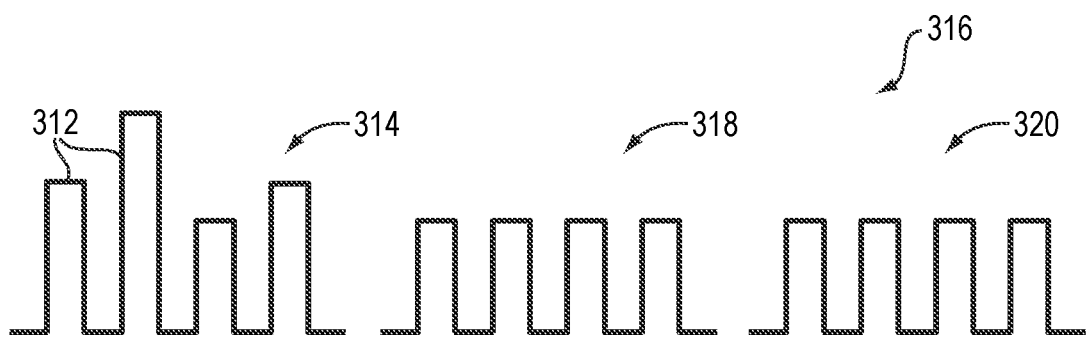
Figure 3E:
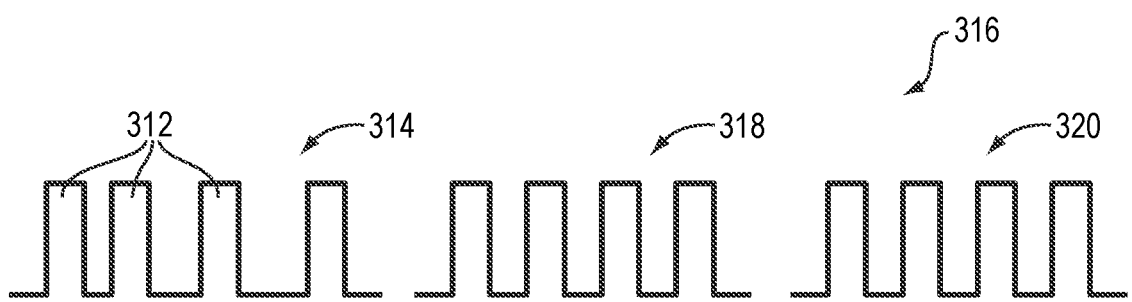
Figure 3F:
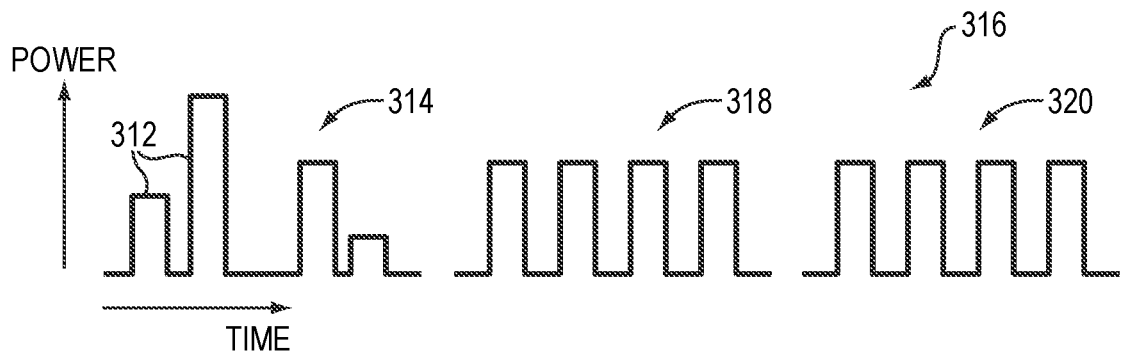
Figure 3G:
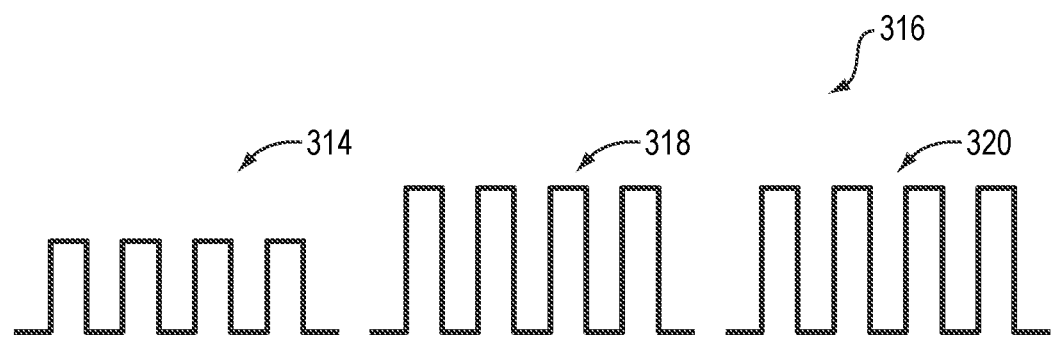
Figure 3H:
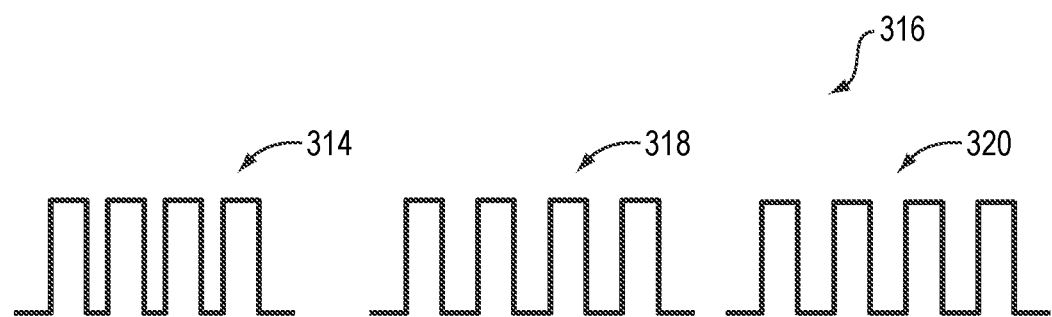
Figure 3I:
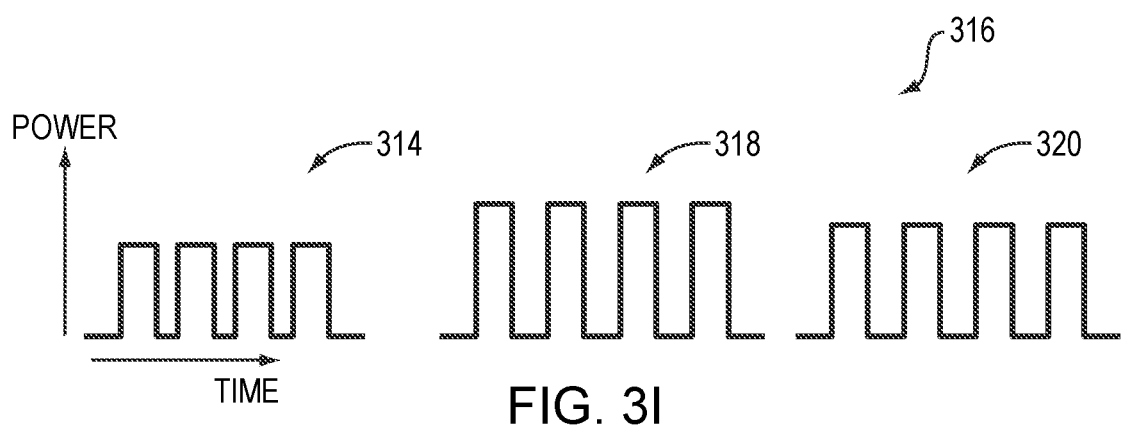

Various parameters of the ultrasound output in the priming sequence(s) may be fixed or may vary. For example, referring again to FIG. 2A, the power and/or frequency of the pulses 204 within the continuous pulse sequence 202 may be fixed; similarly, referring to FIG. 2B, the power and/or frequency of the pulses in a time-separated pulse sequence of the sonication series 212 may be fixed, and the frequency of the sequences 214-218 in the series 212 may be fixed. Alternatively, the power and/or frequency of the pulses within the continuous pulse sequence may vary. For example, FIGS. 3A and 3B depict a varying power and a varying frequency, respectively, of the pulses 302 in a continuous pulse sequence 304. FIG. 3C depicts both power and frequency of the pulses 302 in a continuous pulse sequence 304 vary in the priming stage. In particular, the power may vary from 1 W to 1500 W and the frequency may vary from 50 kHz to 10 MHz. Similarly, the power and/or frequency of the pulses within one time-separated pulse sequence of a sonication series may vary. For example, FIGS. 3D and 3E depict a varying power and frequency, respectively, of the pulses 312 in a time-separated pulse sequence 314 of a sonication series 316. FIG. 3F depicts both power and frequency of the pulses 312 in a time-separated pulse sequence 314 varying in the priming stage. Further, different time-separated pulse sequences 314, 318 of the sonication series 316 may have different power levels (FIGS. 3G and 3I) and/or frequencies (FIGS. 3H and 3I).

Additionally, the transducer 102 may be configured to generate ultrasound pulses having multiple working frequencies in the priming stage; as a result, the priming pulse sequence has a combination (or a mixed frequency) of two or more ultrasound frequencies. The mixed frequency may be fixed within a pulse sequence and/or among different time-separated pulse sequences of a sonication series. Systems and methods for manufacturing and configuring the transducer to provide multiple frequencies and high-power output are described, for example, in U.S. Patent Publ. No. 2016/0114193, the entire disclosure of which is hereby incorporated by reference.

It should be noted that the power and frequency are exemplary parameters that may be fixed or may vary in the priming pulse sequence(s); other parameters such as the sequence length, the ultrasound mechanical index in the target tissue and/or the acoustic beam shape may be fixed or may vary as well and thus are within the scope of the present invention.

Figure 4:
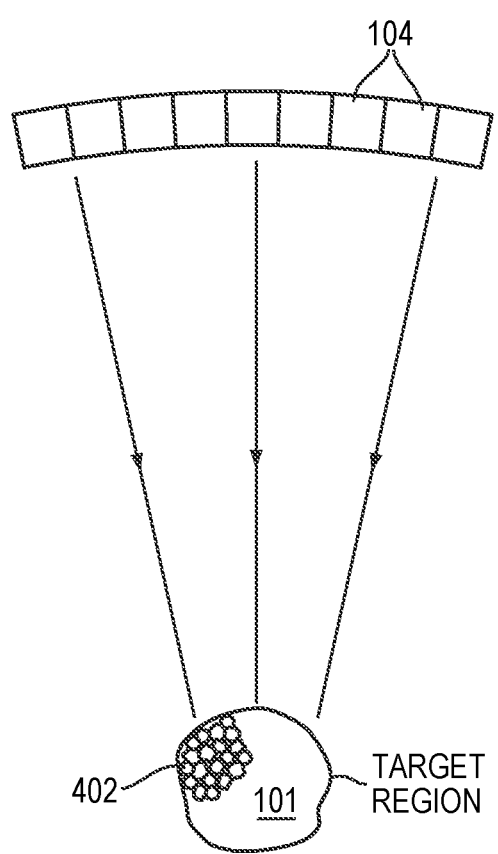
FIG. 4 schematically depicts microbubbles injected and/or generated at the target region in a priming stage in accordance with various embodiments of the current invention.

Referring to FIG. 4, in some embodiments, microbubbles 402 are injected and/or generated in the target region 101 in the priming stage to promote tissue sensitivity. For example, the microbubbles may be generated by applying ultrasound pulses having an energy above a threshold. The microbubbles can be formed due to the negative pressure produced by the propagating ultrasonic pulses or when the heated liquid ruptures and is filled with gas/vapor. Additionally or alternatively, the microbubbles 402 may be introduced into the target region 101 using an administration system 124. For example, the microbubbles may be injected in the form of an ultrasound contrast agent such as SON-OVUE, a suspension of sulfur hexafluoride gas microbubbles. Approaches to generating the microbubbles and/or introducing the microbubbles to the target region 101 are provided, for example, in PCT Publication Nos. WO 2018/020315, WO 2019/116097, WO 2019/058171, WO 2019/116097, and WO 2019/116095, U.S. Patent Publication No. 2019/0083065, and U.S. Pat. No. 10,739,316, the contents of which are incorporated herein by reference.

Depending upon the amplitude and frequency of the applied acoustic field, the microbubbles 402 may oscillate or collapse (this mechanism is called "cavitation"). Cavitation of microbubbles may enhance tissue sensitivity at the target region 101, thereby causing the tissue therein to be heated faster and be ablated more efficiently than would occur in the absence of microbubbles 402. Because cavitation typically involves the production of voids or microbubbles in a liquid, these voids begin to collapse explosively with increasing applied acoustic energy; as the applied energy increases further, the explosions and resulting shock waves (which may be detected as a measure of cavitation intensity) become more violent. Thus, in various embodiments, one or more ultrasound parameters (such as the power, frequency, mechanical index, acoustic beam shape, and sequence length(s)) can be varied in the priming pulse sequence(s) to induce a target range of cavitation that is sufficient to enhance tissue sensitivity while avoiding extreme cavitation that creates significant clinical effects (i.e., a significant temperature increase at the target and/or non-target regions) in the target region. Once the target range of cavitation is achieved, the ultrasound parameter(s) may be fixed to maintain the cavitation level.

In various embodiments, the target range of cavitation is identified prior to or during the priming stage by, for example, ramping up the power of the ultrasound pulses and monitoring the response profile of the microbubbles. The microbubble response can be inferred from the temperature of the target/non-target tissue monitored by the imager 112 and/or the acoustic response of the microbubbles detected by the transducer 102 and/or acoustic-signal detector 126. In one embodiment, the target range of cavitation is identified as having a power range between the power of the pulses that causes gentle and stable cavitation and the power of the pulses that commences formation of a microbubble cloud. Further details about approaches to identifying the target range of cavitation are provided, for example, in U.S. Patent Publication No. 2019/0175954); and approaches to configuring the transducer array for detecting the microbubble response are provided, for example, in PCT Publication No. WO/2019/234497. The entire contents of these applications are incorporated herein by reference.

Besides the applied acoustic energy, the degree of cavitation may also be influenced by the concentration of microbubbles. Thus, in some embodiments, one or more ultrasound parameters (e.g., the power, frequency, mechanical index, acoustic beam shape, and sequence length(s) are optimized (and, in some embodiments, fixed) to maintain the concentration of microbubbles within a fixed range; that range, in turn, may, again, be based on the acoustic response of the microbubbles at the target/non-target regions and/or the temperature of the target/non-target tissue as described above.

Figure 5:
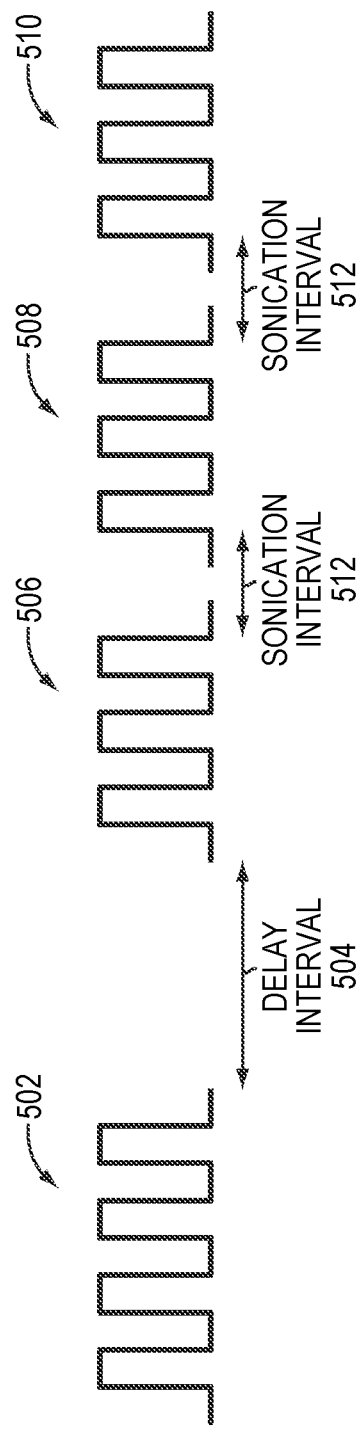
FIG. 5 depicts a priming sonication sequence followed by a delay interval and a series of therapeutic sonication sequences in accordance with various embodiments of the current invention.

Referring to FIG. 5, after the priming pulse sequence(s) 502 ends, the ultrasound transducer 102 may be halted for a delay interval 504 prior to generating a series of one or more treatment sequences 506-510 to the target. As depicted, the treatment sequences have a sonication interval 512 therebetween; the sonication interval 512 may be fixed or may vary throughout the treatment sequences. In one embodiment, the delay interval 504 is preferably longer than the maximal sonication interval 512 by a predetermined factor (e.g., 2 times, 10 times, 50 times or 100 times). For example, the sonication interval 512 may last from 0.1 to 10 sec. and the delay interval may range from 1 sec (when the sonication interval is 0.1 sec) to 3 hours, e.g., 3 min (when the sonication interval is 10 sec).

Additionally, the microbubbles may be generated and/or introduced to the target region 101 after the priming stage. For example, additional microbubbles may be administered during treatment for improving focusing properties of the ultrasound focused beam and/or assisting tissue disruption or necrosis. Approaches to utilizing microbubbles for improving focusing properties are provided, for example, in U.S. Patent Publication No. 2019/0175954 and PCT Publication No. WO 2020/128615; and approaches to utilizing microbubbles for assisting tissue disruption or necrosis are provided, for example, in U.S. Patent Publication Nos. 2019/0001154 and 2020/0139158 and PCT Publication No. WO 2019/002949. The entire contents of these applications are incorporated herein by reference.

Figure 6:
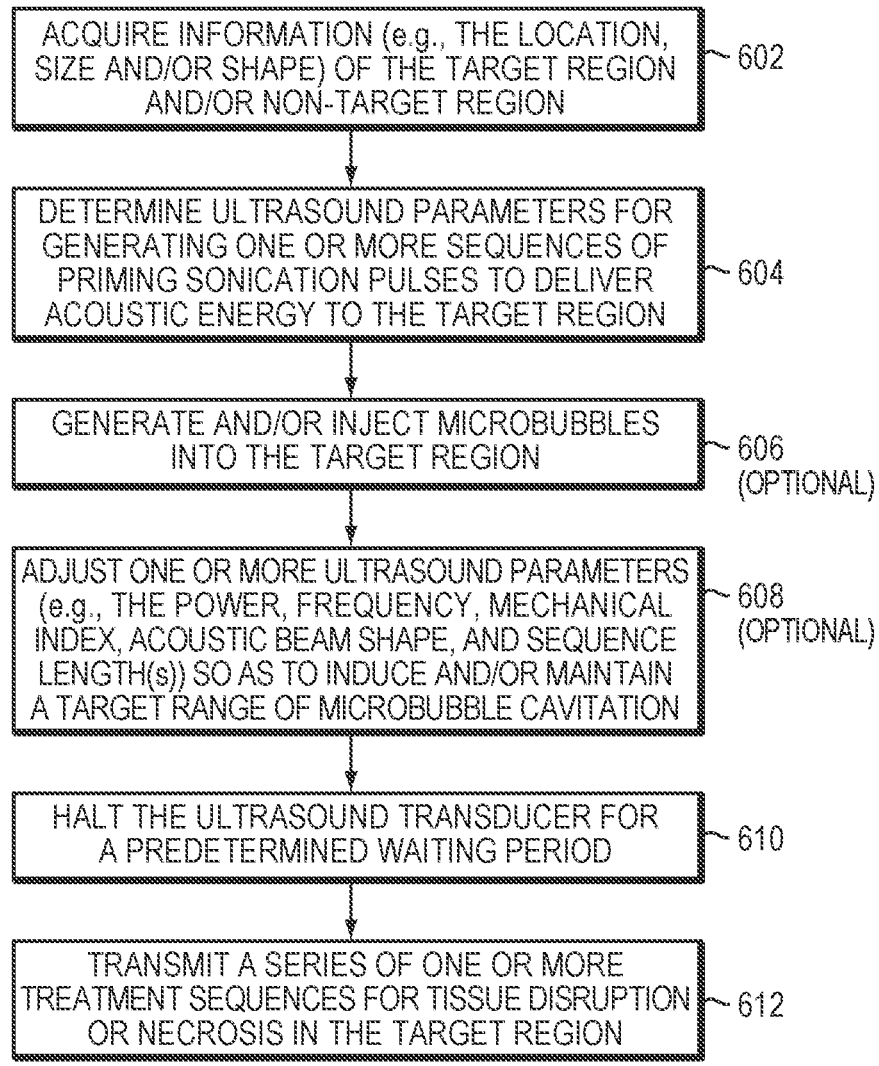
FIG. 6 is a flow chart illustrating an exemplary approach for treating target tissue in accordance with various embodiments of the current invention.

FIG. 6 is a flow chart illustrating an exemplary approach 600 for enhancing tissue sensitivity, thereby permitting effective ultrasound therapy of the target tissue while avoiding damage to the non-target tissue in accordance herewith. In a first step 602, an imager (e.g., MRI device) is activated to acquire information (such as the location, size and/or shape) of the target region and/or non-target region. In a second step 604, based on the acquired information, one or more sequences of priming sonication pulses can be generated to apply acoustic energy to the target region for enhancing tissue sensitivity therein. In addition, microbubbles may be optionally generated and/or injected into the target region to further enhance tissue sensitivity (step 606). If the microbubbles are used in the priming stage, one or more ultrasound parameters (such as the power, frequency, mechanical index, acoustic beam shape, and sequence length(s)) may be adjusted so as to induce and/or maintain a target range of cavitation that is sufficient to enhance tissue sensitivity while avoiding extreme cavitation that creates significant clinical effects (i.e., a significant temperature increase at the target and/or non-target regions) in the target region (step 608). Once the priming stage is complete, the ultrasound transducer may be halted for a predetermined delay interval (step 610). Thereafter, the ultrasound transducer may be activated to transmit a series of one or more treatment sequences for tissue disruption or necrosis in the target region (step 612). Again, the microbubbles may be optionally introduced to the target during treatment for assisting tissue disruption or necrosis and/or improving focusing properties of the ultrasound focused beam. Optionally, the priming sequence and/or the treatment sequence may be guided by the imager 112.

Accordingly, various embodiments apply the priming sequence of sonication pulses prior to application of the therapeutic sonication pulses to the target tissue; this approach may advantageously enhance sensitivity of various types of target tissue to acoustic energy at various frequencies. As a result, the acoustic energy required for tissue disruption/necrosis in the target region can be reduced. Accordingly, various embodiments effectively reduce the required acoustic energy from the ultrasound transducer to provide effective target therapy while avoiding damage to the non-target tissue.

In general, functionality for performing an ultrasound treatment procedure, including, for example, generating one or more priming sequences of sonication pulses, adjust parameters of the priming sonication sequence(s), generating microbubbles, applying sonications to cause microbubble cavitation, and generating a series of therapeutic sequences of sonication pulses as described above, whether integrated within a controller of the imager, and/or an ultrasound system, or provided by a separate external controller, may be structured in one or more modules implemented in hardware, software, or a combination of both. For embodiments in which the functions are provided as one or more software programs, the programs may be written in any of a number of high level languages such as PYTHON, JAVA, C, C++, C#, BASIC, various scripting languages, and/or HTML. Additionally, the software can be implemented in an assembly language directed to the microprocessor resident on a target computer (e.g., the controller); for example, the software may be implemented in Intel 80x86 assembly language if it is configured to run on an IBM PC or PC clone. The software may be embodied on an article of manufacture including, but not limited to, a floppy disk, a jump drive, a hard disk, an optical disk, a magnetic tape, a PROM, an EPROM, EEPROM, field-programmable gate array, or CD-ROM. Embodiments using hardware circuitry may be implemented using, for example, one or more FPGA, CPLD or ASIC processors.

In addition, the term "controller" used herein broadly includes all necessary hardware components and/or software modules utilized to perform any functionality as described above; the controller may include multiple hardware components and/or software modules and the functionality can be spread among different components and/or modules. Further, the phased-array operation is optional (simple transducers are acceptable for some applications), as is image guidance. If imaging is employed, the treatment sequence, the priming sequence or both may be guided thereby. The image modality may be Mill, as discussed, or computed tomography (CT), X-ray, positron-emission tomography (PET), single-photon emission computed tomography (SPECT), or infrared imaging. The imaging device may produce 1D, 2D, 3D and/or 4D images.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. A system for treating target tissue, the system comprising:
    an ultrasound transducer for delivering acoustic energy to the target tissue; and
    a controller, configured to (i) generate a priming sequence of sonication pulses for driving the ultrasound transducer to deliver acoustic energy to the target tissue in accordance with the priming sequence, (ii) pause driving the ultrasound transducer for a delay interval, and (iii) generate a series of treatment sequences of sonication pulses for driving the ultrasound transducer to deliver acoustic energy to the target tissue in accordance with the series of treatment sequences,
    wherein the treatment sequences have sonication intervals therebetween and the delay interval is larger than a largest sonication interval by a predetermined factor, and wherein the delay interval occurs between steps (i) and (iii).

2. The system of claim 1, further comprising an administration device for administering an ultrasound contrast agent for action at the target tissue.

3. The system of claim 2, wherein the controller is further configured to operate the administration device to administer the ultrasound contrast agent during the priming sequence and/or the treatment sequence.

4. The system of claim 1, wherein the priming sequence has at least one fixed parameter selected from a frequency, a power, a mechanical index in the target tissue and an acoustic beam shape.

5. The system of claim 4, wherein the controller is further configured to determine a value of the at least one fixed parameter for maintaining a target concentration of microbubbles at the target tissue.

6. The system of claim 1, wherein the priming sequence has at least one varying parameter selected from a frequency, a power, a mechanical index in target tissue and an acoustic beam shape.

7. The system of claim 6, wherein the controller is further configured to determine a value of the at least one varying parameter for (i) initiating microbubble cavitation in the target tissue, (ii) maintaining a target range of microbubble cavitation at the target tissue, and/or (iii) avoiding formation of a microbubble cloud in the target tissue.

8. The system of claim 7, wherein the controller is further configured to determine the target range of microbubble cavitation based at least in part on an acoustic response from the target tissue.

9. The system of claim 1, further comprising at least one acoustic-signal detector, the controller being further configured to adjust a parameter associated with the priming sequence based on an acoustic response from the target tissue detected by the at least one acoustic-signal detector.

10. The system of claim 1, wherein the priming sequence has a mixed frequency.

11. The system of claim 1, further comprising at least one imaging device for guiding at least one of the priming sequence or the treatment sequences.

12. The system of claim 11, wherein the imaging device comprises at least one of an ultrasound, an MRI, a CT, an X-Ray, a PET, an SPECT or an infrared imaging device.

13. The system of claim 12, wherein the imaging device produces at least one of 1D, 2D, 3D or 4D images.

14. The system of claim 1, wherein the predetermined factor is at least ten.

15. The system of claim 1, wherein the predetermined factor is at least two.

16. The system of claim 1, wherein the transducer is a phased-array transducer.

17. A method of treating target tissue comprising:
    generating a priming sequence of sonication pulses for delivering acoustic energy to the target tissue;
    pausing generation of the sonication pulses for a delay interval; and
    generating a series of treatment sequences of sonication pulses for delivering acoustic energy to the target tissue,
    wherein the treatment sequences have sonication intervals therebetween and the delay interval is larger than a largest sonication interval by a predetermined factor, and wherein the delay interval occurs after generating the priming sequence and before generating the series of treatment sequences.

18. A system for treating target tissue, the system comprising:
- an ultrasound transducer for delivering acoustic energy to the target tissue;
- an administration device for administering an ultrasound contrast agent at the target tissue; and
- a controller, configured to (i) generate a priming sequence of sonication pulses for driving the ultrasound transducer to deliver acoustic energy to the target tissue in accordance with the priming sequence, (ii) operate the administration device to administer the ultrasound contrast agent during the priming sequence, (iii) pause generation of the sonication pulses for a delay interval, and (iv) subsequent to the delay interval, generate a treatment sequence of sonication pulses for driving the ultrasound transducer to deliver acoustic energy to the target tissue in accordance with the treatment sequence.

19. The system of claim 18, wherein the priming sequence has at least one fixed parameter selected from a frequency, a power, a mechanical index in the target tissue and an acoustic beam shape.

20. The system of claim 19, wherein the controller is further configured to determine a value of the at least one fixed parameter for maintaining a target concentration of microbubbles at the target tissue.

21. The system of claim 18, wherein the priming sequence has at least one varying parameter selected from a frequency, a power, a mechanical index in target tissue and an acoustic beam shape.

22. The system of claim 21, wherein the controller is further configured to determine a value of the at least one varying parameter for (i) initiating microbubble cavitation in the target tissue, (ii) maintaining a target range of microbubble cavitation at the target tissue, and/or (iii) avoiding formation of a microbubble cloud in the target tissue.

23. The system of claim 22, wherein the controller is further configured to determine the target range of microbubble cavitation based at least in part on an acoustic response from the target tissue.

24. The system of claim 18, further comprising at least one acoustic-signal detector, the controller being further configured to adjust a parameter associated with the priming sequence based on an acoustic response from the target tissue detected by the at least one acoustic-signal detector.

25. The system of claim 18, wherein the priming sequence has a mixed frequency.

26. The system of claim 18, further comprising at least one imaging device for guiding at least one of the priming sequence or the treatment sequence.

27. The system of claim 26, wherein the imaging device comprises at least one of an ultrasound, an MRI, a CT, an X-Ray, a PET, an SPECT or an infrared imaging device.

28. The system of claim 26, wherein the imaging device produces at least one of 1D, 2D, 3D or 4D images.

29. The system of claim 18, wherein the controller is further configured to operate the administration device to administer the ultrasound contrast agent during the treatment sequence.

30. The system of claim 18, wherein the transducer is a phased-array transducer.

31. A method of treating target tissue comprising:
- generating a priming sequence of sonication pulses for delivering acoustic energy to the target tissue in accordance with the priming sequence;
- administering an ultrasound contrast agent during the priming sequence;
- pausing generation of the sonication pulses for a delay interval; and
- subsequent to the delay interval, generating a treatment sequence of sonication pulses for delivering acoustic energy to the target tissue in accordance with the treatment sequence.

* * * * *